(12) United States Patent
Kikuchi et al.

(10) Patent No.: US 8,524,921 B2
(45) Date of Patent: Sep. 3, 2013

(54) LIQUID TETRACARBOXYLIC DIANHYDRIDES AND PROCESS FOR THE PREPARATION THEREOF

(75) Inventors: Tooru Kikuchi, Hitachi (JP); Hayato Kotani, Tsukuba (JP); Katsuyuki Masuda, Chikusei (JP); Toshihiko Takasaki, Tsukuba (JP)

(73) Assignee: Hitachi Chemical Co., Ltd., Tokyo (JP)

( * ) Notice: Subject to any disclaimer, the term of this patent is extended or adjusted under 35 U.S.C. 154(b) by 12 days.

(21) Appl. No.: 13/202,067

(22) PCT Filed: Dec. 8, 2009

(86) PCT No.: PCT/JP2009/070556
§ 371 (c)(1),
(2), (4) Date: Aug. 17, 2011

(87) PCT Pub. No.: WO2010/095329
PCT Pub. Date: Aug. 26, 2010

(65) Prior Publication Data
US 2011/0301362 A1  Dec. 8, 2011

(30) Foreign Application Priority Data
Feb. 18, 2009  (JP) .................. P2009-035404

(51) Int. Cl.
C07D 493/00  (2006.01)
C07D 307/77  (2006.01)
C07F 7/08  (2006.01)

(52) U.S. Cl.
USPC .................................. 549/214; 549/237

(58) Field of Classification Search
USPC .................................................... 549/214
See application file for complete search history.

(56) References Cited

U.S. PATENT DOCUMENTS

| 4,381,396 A | * | 4/1983 | Ryang .......................... 549/214 |
| 4,542,226 A | | 9/1985 | Eddy et al. |

(Continued)

FOREIGN PATENT DOCUMENTS

| JP | 59-501208 A | 7/1984 |
| JP | 60-197721 A | 10/1985 |

(Continued)

OTHER PUBLICATIONS

Andre et al. (Polymer 42 (2001) 5505-5513).*

(Continued)

*Primary Examiner* — Noble Jarrell
*Assistant Examiner* — Valerie Rodriguez-Garcia
(74) *Attorney, Agent, or Firm* — Antonelli, Terry, Stout & Kraus, LLP.

(57) ABSTRACT

The invention relates to a tetracarboxylic dianhydride represented by the following formula (1).

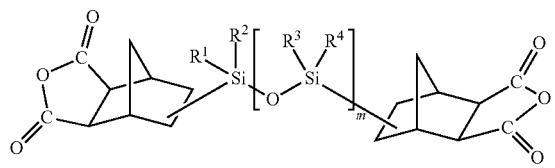

(1)

[In formula (1) $R^1$, $R^2$, $R^3$ and $R^4$ each independently represent an alkyl group having from 1 to 5 carbon atoms, m represents a number from 1 to 30, all of the silicon atoms bonding to the norbornane rings are in an exo-configuration with respect to the norbornane rings, and all of the dicarboxylic anhydride groups bonding to the norbornane rings are in an exo-configuration with respect to the norbornane rings.]

2 Claims, 6 Drawing Sheets

(56) References Cited

U.S. PATENT DOCUMENTS

| | | | |
|---|---|---|---|
| 4,582,886 | A | 4/1986 | Ryang |
| 7,022,410 | B2 | 4/2006 | Tonapi et al. |
| 7,279,223 | B2 | 10/2007 | Rubinsztajn et al. |
| 2005/0129956 | A1* | 6/2005 | Rubinsztajn et al. ......... 428/413 |
| 2008/0001140 | A1 | 1/2008 | Haitko et al. |

FOREIGN PATENT DOCUMENTS

| | | |
|---|---|---|
| JP | 60-210624 A | 10/1985 |
| JP | 61-056189 A | 3/1986 |
| JP | 03-56490 A | 3/1991 |
| JP | 05-320172 A | 12/1993 |
| JP | 2003-002951 A | 1/2003 |
| JP | 2007-145966 A | 6/2007 |
| JP | 2007-515524 A | 6/2007 |
| JP | 2007-516331 A | 6/2007 |

OTHER PUBLICATIONS

Written Opinion of the International Searching Authority, directed to International Patent Application No. PCT/JP2009/070556, 6 pages, dated Sep. 22, 2011.

Elsevier Sequoia S. A., Lausanne, "Journal of Organometallic Chemistry, vol. 402, Issue 2", 1991, p. 145-p. 153.

Trofimov, A. E. et al., "Russian Journal of General Chemistry, vol. 68, No. 4" 1998, p. 572-p. 577.

Li, H. et al, "Polymer International, vol. 54, Issue 10" p. 1416-p. 1421, (2005).

Wu, S. et al., "High Performance Polymers, 20", 2008, p. 281-p. 295.

International Search Report, directed to International Patent Application No. PCT/JP2009/070556, 2 pages.

* cited by examiner

LIQUID TETRACARBOXYLIC DIANHYDRIDES AND PROCESS FOR THE PREPARATION THEREOF

TECHNICAL FIELD

The present invention relates to novel liquid tetracarboxylic dianhydrides and to a process for preparation thereof.

BACKGROUND ART

Research and development of transparent materials is actively ongoing in the field of optoelectronics, which includes optical devices, displays and optical data transmission, and applications of such materials are being investigated. Wavelengths of 300-500 nm are being aggressively pursued with the aim of achieving greater energy density and efficiency in the field.

Epoxy resins and polyimide resins are commonly known organic materials that are used in electronic devices, and aromatic resins are employed for purposes of heat resistance. However, aromatic resins are limited in their use as transparent materials, because of their absorption in the aforementioned wavelength range. Thus, the development of non-aromatic transparent materials with high heat resistance is desired. Heat-resistant transparent materials employed in the field of optoelectronics must exhibit adhesion with silicon substrates and glass panels, as well as solubility in general-purpose solvents and compatibility with other materials, and they are preferred to be liquid for easier handling.

In order to obtain epoxy resins and polyimide resins exhibiting such properties, research is being conducted on the use of alicyclic tetracarboxylic dianhydrides as curing agents for epoxy resins or components of polyimide resins.

For example, Patent Literatures 1-3 and Non-patent Literatures 1-3 disclose tetracarboxylic dianhydrides represented by the following structural formula (4), synthesized from 5-norbornene-2,3-dicarboxylic anhydride and tetramethyldisiloxane or dimethylchlorosilane, as well as application examples of the same.

[Chemical Formula 1]

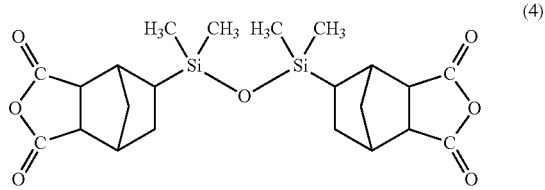

(4)

Also, Patent Literature 4 and Non-patent Literature 4 disclose tetracarboxylic dianhydrides represented by the following structural formula (5), synthesized from 5-norbornene-2,3-dicarboxylic anhydride and hexamethyltrisiloxane, as well as application examples of the same.

[Chemical Formula 2]

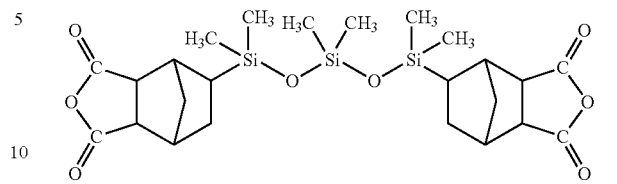

(5)

CITATION LIST

Patent Literature

Patent Literature 1: JP 59-501208 W
Patent Literature 2: JP 61-56189 A
Patent Literature 3: JP 60-210624 A
Patent Literature 4: JP 2007-515524 W

Non-Patent Literature

Non-patent Literature 1: Journal of Organometallic Chemistry, 402(2), 145-53 (1991)
Non-patent Literature 2: Russian Journal of General Chemistry, Vol. 68, No. 4, 572-577 (1998)
Non-patent Literature 3: Polymer International, 54(10), 1416-1421 (2005)
Non-patent Literature 4: High Performance Polymers, 20, 281-295 (2008)

SUMMARY OF INVENTION

Technical Problem

The tetracarboxylic dianhydrides described in the aforementioned patent literature and non-patent literature, however, are all white crystalline solids with high melting points. Thus, when it is attempted to use such tetracarboxylic dianhydrides as starting materials for synthesis of polyimide resins, it is often difficult to exhibit excellent properties, or cyclic oligomer by-products may result. In addition, because these tetracarboxylic dianhydrides have high melting points, attempts to employ them as epoxy resin curing agents by admixture with epoxy resins in the preparation of epoxy resin compositions have required heating to near the melting points of the tetracarboxylic dianhydrides, and the epoxy resin compositions sometimes have reduced storage stability.

It is therefore an object of the present invention to provide tetracarboxylic dianhydrides which are liquid at room temperature and have excellent manageability, as well as a process for their preparation.

Solution to Problem

Based on investigation by the present inventors, it has been confirmed that the silicon-containing tetracarboxylic dianhydrides with norbornane skeletons disclosed in the aforementioned patent literature and non-patent literature have endo-type stereostructures of the dicarboxylic anhydride groups bonded to the norbornane rings. These tetracarboxylic dianhydrides have bent molecular structures, high melting points and solid states near room temperature.

The CAS Registry Numbers corresponding to the molecular formula $C_{22}H_{30}O_7Si_2$ of the tetracarboxylic dianhydrides represented by chemical formula (4) above include [86531-

37-5], which has no proposed stereostructure, and [129646-52-2], [217448-20-9], [217448-22-1] and [869277-10-1], which have proposed stereo structures. The CAS Registry Numbers corresponding to the molecular formula $C_{24}H_{36}O_8Si_3$ of the tetracarboxylic dianhydrides represented by chemical formula (5) above include [569669-52-9], which has no proposed stereostructure, and [1042977-06-9] which has a proposed stereostructure.

Specifically, Non-patent Literature 1 discloses 5,5'-exo-(1,1,3,3-tetramethyldisiloxane-1,3-diyl)bisbicyclo[2.2.1] heptane-endo-2,3-dicarboxylic anhydride represented by chemical formula (4a) below, which is a tetracarboxylic dianhydride corresponding to CAS Registry Number [129646-52-2]. The melting point of this tetracarboxylic dianhydride is 126-153° C.

[Chemical Formula 3]

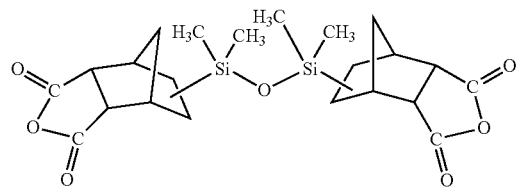

(4a)

Also, Non-patent Literature 2 discloses tetracarboxylic dianhydrides corresponding to CAS Registry Numbers [217448-20-9] and [217448-22-1], while Non-patent Literature 3 discloses a tetracarboxylic dianhydride corresponding to CAS Registry Number [869277-10-1], wherein the stereostructure of the dicarboxylic anhydride group of the norbornane ring has an endo-configuration.

Non-patent Literature 4 discloses 5,5'-exo-(1,1,3,3,5,5-hexamethyltrisiloxane-1,5-diyl)bisbicyclo[2.2.1]heptane-endo-2,3-dicarboxylic anhydride represented by chemical formula (5a) below, which is a tetracarboxylic dianhydride corresponding to CAS Registry Number [1042977-06-9]. The melting point of this tetracarboxylic dianhydride is 133.4-133.9° C.

[Chemical Formula 4]

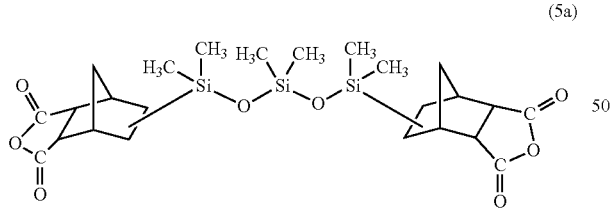

(5a)

Patent Literatures 1-4, on the other hand, do not specifically mention the stereostructure of the 5-norbornene-2,3-dicarboxylic anhydride used as the starting material for synthesis, or the stereostructure of the dicarboxylic anhydride group bonded to the norbornane ring of the synthesized tetracarboxylic dianhydride. Regarding the obtained tetracarboxylic dianhydride, however, it is stated in Patent Literature 1 that it is a white crystalline solid, in Patent Literature 2 that it has a melting point of 125-148° C., in Patent Literature 3 that it is a white crystalline solid, and in Patent Literature 4 that it is a white solid substance. It is therefore believed that these tetracarboxylic dianhydrides also have endo-configurations for the stereostructures of the dicarboxylic anhydride groups of the norbornane rings.

As a result of much diligent research in order to achieve the object stated above, the present inventors have found that a liquid with no melting point results if the stereo structure of the dicarboxylic anhydride group of the norbornane ring in a silicon-containing tetracarboxylic dianhydride with a norbornane skeleton is an exo-structure, and the invention has been completed upon this finding.

Specifically, the invention provides a tetracarboxylic dianhydride represented by the following formula (1).

[Chemical Formula 5]

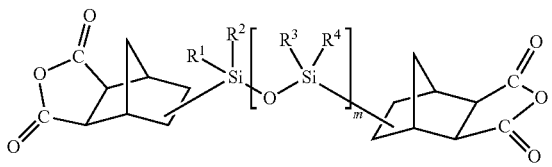

(1)

In formula (1), $R^1$, $R^2$, $R^3$ and $R^4$ each independently represent an alkyl group having from 1 to 5 carbon atoms, and m represents a number from 1 to 30. Incidentally, all of the silicon atoms bonding to the norbornane rings in formula (1) are in an exo-configuration with respect to the norbornane rings, and all of the dicarboxylic anhydride groups bonding to the norbornane rings are in an exo-configuration with respect to the norbornane rings.

The tetracarboxylic dianhydride preferably has a viscosity of 0.1-45000 Pa·s at 25° C.

The present invention further provides a process for preparation of the tetracarboxylic dianhydride of the invention, the process comprising a step of hydrosilylation reaction between a 5-norbornene-exo-2,3-dicarboxylic anhydride represented by the following chemical formula (2) and a siloxane compound represented by the following formula (3).

[Chemical Formula 6]

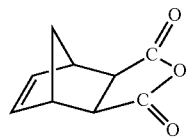

(2)

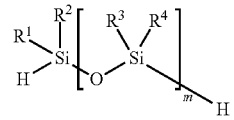

(3)

In formula (3), $R^1$, $R^2$, $R^3$ and $R^4$ each independently represent an alkyl group having from 1 to 5 carbon atoms, and m represents a number from 1 to 30.

This preparation process allows easy production of a tetracarboxylic dianhydride represented by formula (1).

Advantageous Effects of Invention

According to the invention it is possible to provide a silicon-containing tetracarboxylic dianhydride having a norbornane skeleton, which is liquid at room temperature and has excellent manageability, as well as a process for preparation of the same. The tetracarboxylic dianhydride of the invention can be suitably used as a curing agent for epoxy resins, or as a tetracarboxylic anhydride component for synthesis of polyimide resins. In synthesis of a polyimide resin using the tetracarboxylic dianhydride of the invention, it is possible to inhibit by-production of cyclic oligomers.

DESCRIPTION OF EMBODIMENTS

Figure 1:
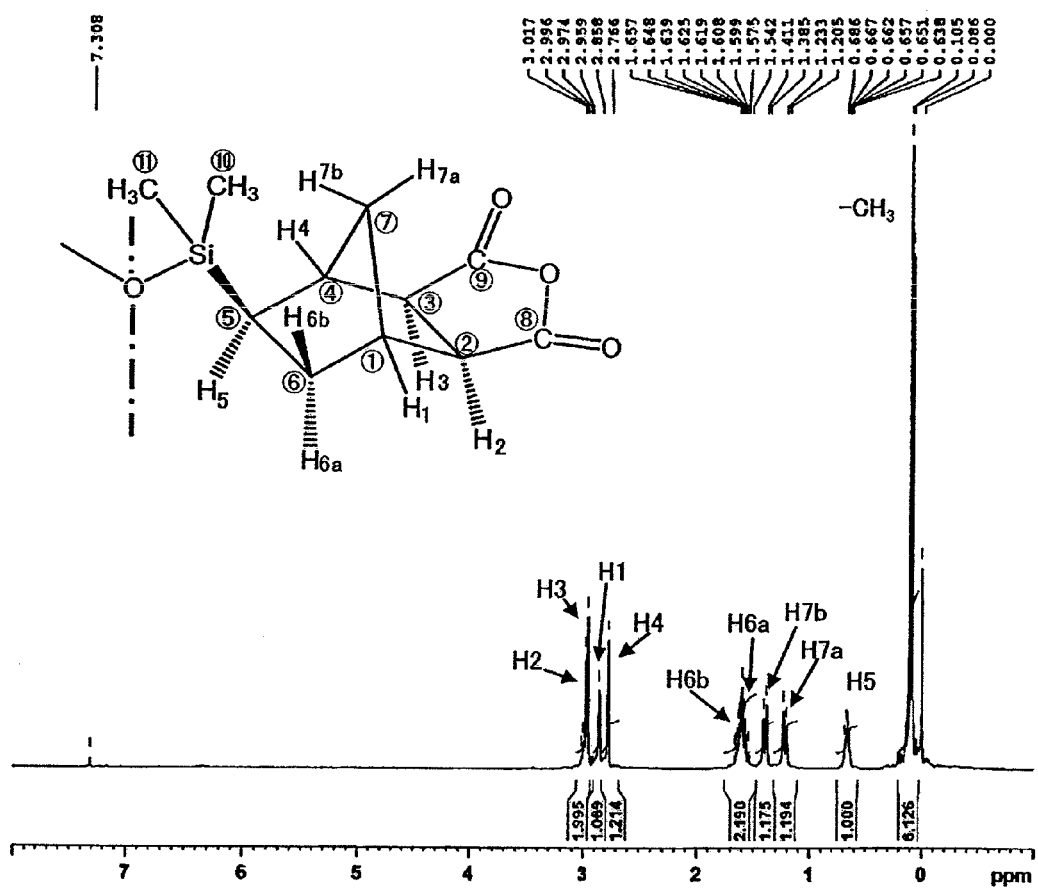
FIG. 1 shows the $^1$H-NMR spectrum of the tetracarboxylic dianhydride of Example 1.

Preferred embodiments of the invention will now be described in detail. However, the present invention is not limited to the embodiments described below.

The tetracarboxylic dianhydride of this embodiment is represented by formula (1) below. The tetracarboxylic dianhydride represented by formula (1) has a structure in which norbornane-exo-2,3-dicarboxylic anhydride is bonded at both ends of a polysiloxane. Specifically, all of the silicon atoms bonding to the norbornane rings in the tetracarboxylic dianhydride of this embodiment are in an exo-configuration with respect to the norbornane rings, and all of the dicarboxylic anhydride groups bonding to the norbornane rings are in an exo-configuration with respect to the norbornane rings. The tetracarboxylic dianhydride of this embodiment will also be referred to hereunder as "exo-exo type tetracarboxylic dianhydride".

[Chemical Formula 7]

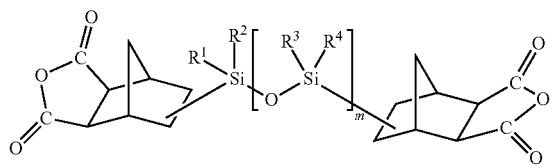

(1)

In formula (1), $R^1$, $R^2$, $R^3$ and $R^4$ each independently represent an alkyl group having from 1 to 5 carbon atoms, and are most preferably methyl groups. Also, m represents a number from 1 to 30, preferably from 1 to 15, more preferably from 1 to 10 and even more preferably from 1 to 5. Incidentally, the tetracarboxylic dianhydride represented by formula (1) may be a tetracarboxylic dianhydride having a single value for m, or a mixture of tetracarboxylic dianhydrides with different m values.

The exo-exo type tetracarboxylic dianhydride is a liquid at room temperature (25° C.), and the viscosity varies depending on the value of m in formula (1), with a larger m value tending to result in lower viscosity, and formation of a glassy solid without crystalline solidification even upon cooling. For example, when $R^1$, $R^2$, $R^3$ and $R^4$ are methyl groups and m is 1 in formula (1), the viscosity of the exo-exo type tetracarboxylic dianhydride is 2960 Pa·s at 40° C. (42500 Pa·s at 25° C.), when m is 2 it is 38.4 Pa·s at 40° C. (220 Pa·s at 25° C.), and when m is 4 it is 3.95 Pa·s at 25° C. That is, the 25° C. viscosity of the exo-exo type tetracarboxylic dianhydride is preferably 0.1-45000 Pa·s when $R^1$, $R^2$, $R^3$ and $R^4$ are methyl groups in formula (1). In this viscosity range, mixture with epoxy resins is facilitated without heating at high temperatures of 100° C. and above, and it is possible to produce an epoxy resin composition with excellent storage stability.

The exo-exo type tetracarboxylic dianhydride of this embodiment can be obtained by a method comprising a step of hydrosilylation between a 5-norbornene-exo-2,3-dicarboxylic anhydride represented by chemical formula (2) below and a siloxane compound represented by formula (3) below.

[Chemical Formula 8]

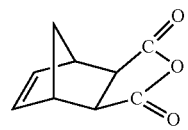

(2)

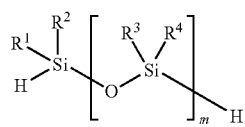

(3)

In formula (3), $R^1$, $R^2$, $R^3$ and $R^4$ each independently represent an alkyl group having from 1 to 5 carbon atoms, and are most preferably methyl groups. Also, m represents a number from 1 to 30, preferably from 1 to 15, more preferably from 1 to 10 and even more preferably from 1 to 5. The siloxane compound represented by formula (3) may be a siloxane compound with a single value for m, or a mixture of siloxane compounds with different m values.

When $R^1$, $R^2$, $R^3$ and $R^4$ are methyl groups and m is 1 in formula (1), it is possible to obtain a tetracarboxylic dianhydride represented by chemical formula (6) below, i.e. 5,5'-exo-(1,1,3,3-tetramethyldisiloxane-1,3-diyl)bisbicyclo[2.2.1]heptan e-exo-2,3-dicarboxylic anhydride.

[Chemical Formula 9]

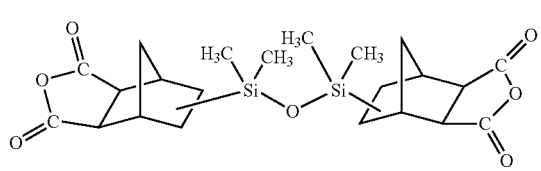

(6)

The exo-exo type tetracarboxylic dianhydride represented by chemical formula (6) is an isomer mixture of tetracarboxylic dianhydrides represented by chemical formulas (6a), (6b) and (6c) below.

In the tetracarboxylic dianhydride represented by chemical formula (6a), the two silicon atoms are in an exo-configuration with respect to the norbornane rings, and are in the R-configuration and S-configuration, in stereochemical notation.

[Chemical Formula 10]

(6a)

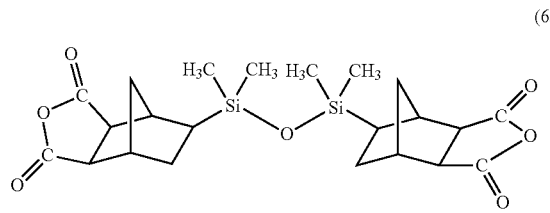

In the tetracarboxylic dianhydride represented by chemical formula (6b), both of the silicon atoms are in an exo-configuration with respect to the norbornane rings, and both are in the R-configuration, in stereochemical notation.

[Chemical Formula 11]

(6b)

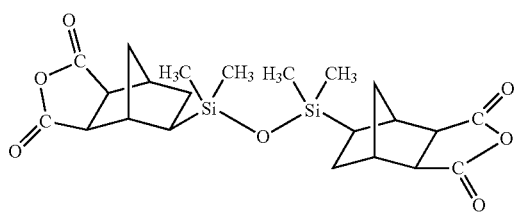

In the tetracarboxylic dianhydride represented by chemical formula (6c), both of the silicon atoms are in an exo-configuration with respect to the norbornane rings, and both are in the S-configuration, in stereochemical notation.

[Chemical Formula 12]

(6c)

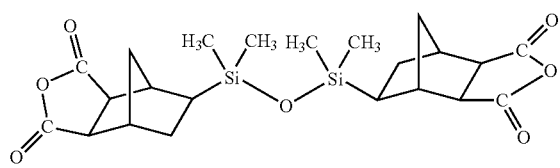

When $R^1$, $R^2$, $R^3$ and $R^4$ are methyl groups and m is 2 in formula (1), it is possible to obtain an exo-exo type tetracarboxylic dianhydride represented by chemical formula (7) below, i.e. 5,5'-exo-(1,1,3,3,5,5-hexamethyltrisiloxane-1,5-diyl)bisbicyclo [2.2.1] heptane-exo-2,3-dicarboxylic anhydride.

[Chemical Formula 13]

(7)

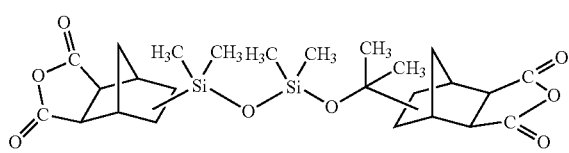

The exo-exo type tetracarboxylic dianhydride represented by chemical formula (7) is an isomer mixture of tetracarboxylic dianhydrides represented by chemical formulas (7a), (7b) and (7c) below.

In the tetracarboxylic dianhydride represented by chemical formula (7a), the two silicon atoms at the terminals are in an exo-configuration with respect to the norbornane rings, and are in the R-configuration and S-configuration, in stereochemical notation.

[Chemical Formula 14]

(7a)

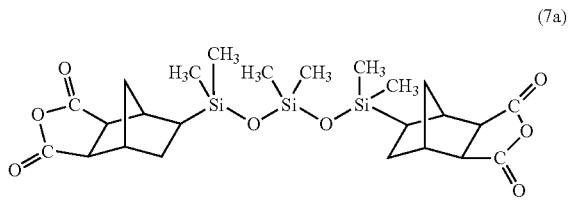

In the tetracarboxylic dianhydride represented by chemical formula (7b), both of the silicon atoms at the terminals are in an exo-configuration with respect to the norbornane rings, and both are in the R-configuration, in stereochemical notation.

[Chemical Formula 15]

(7b)

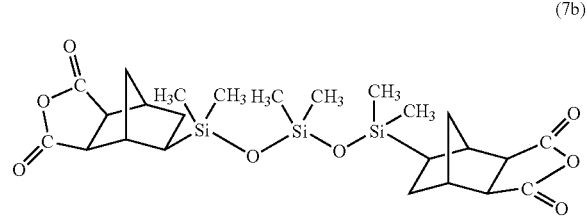

In the tetracarboxylic dianhydride represented by chemical formula (7c), both of the silicon atoms at the terminals are in an exo-configuration with respect to the norbornane rings, and both are in the S-configuration, in stereochemical notation.

[Chemical Formula 16]

(7c)

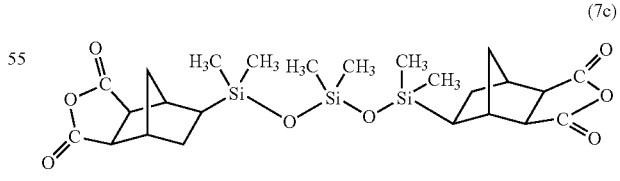

When $R^1$, $R^2$, $R^3$ and $R^4$ are methyl groups and m is 4 in formula (1), it is possible to obtain an exo-exo type tetracarboxylic dianhydride represented by chemical formula (8) below, i.e. 5,5'-exo-(1,1,3,3,5,5,7,7,9,9-decamethylpentasiloxane-1,9-diyl)bisbicycl o[2.2.1]heptane-exo-2,3-dicarboxylic anhydride.

[Chemical Formula 17]

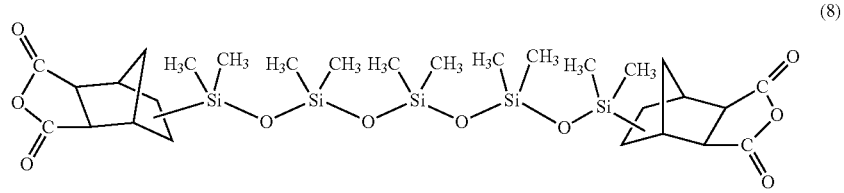

(8)

This case as well is an isomer mixture of the R,S-configuration, R,R-configuration and S,S-configuration, similar to chemical formulas (6) and (7).

The 5-norbornene-exo-2,3-dicarboxylic anhydride represented by chemical formula (2) above is available as a commercial product, and for example, it is sold as a reagent by Aldrich Co. It can also be synthesized by thermal isomerization of 5-norbornene-endo-2,3-dicarboxylic anhydride obtained by Diels-Alder reaction of cyclopentadiene and maleic anhydride. In the thermal isomerization reaction, the 5-norbornene-exo-2,3-dicarboxylic anhydride and 5-norbornene-endo-2,3-dicarboxylic anhydride are in a mixture of 1:1, but the relatively low solubility of 5-norbornene-exo-2,3-dicarboxylic anhydride in toluene or acetone can be utilized to isolate the 5-norbornene-exo-2,3-dicarboxylic anhydride by recrystallization.

Examples of siloxane compounds represented by formula (3) include 1,1,3,3-tetramethyldisiloxane, 1,1,3,3,5,5-hexamethyltrisiloxane, 1,1,3,3,5,5,7,7-octamethyltetrasiloxane and 1,1,3,3,5,5,7,7,9,9-decamethylpentasiloxane, as commercially available products. Mixtures of these siloxane compounds are also commercially available, and may likewise be used.

The content of the siloxane compound represented by formula (3) used for synthesis of an exo-exo type tetracarboxylic dianhydride represented by formula (1) is most preferably, in theoretical terms, 1 mol to 2 mol of the 5-norbornene-exo-2,3-dicarboxylic anhydride represented by chemical formula (2), but it is preferably 0.99-1.01 mol in consideration of weighing error. If the content of the siloxane compound represented by formula (3) exceeds 1.01 mol, the mono compound, having only one 5-norbornene-exo-2,3-dicarboxylic anhydride added to the siloxane compound represented by formula (3), will remain, and effort will be necessary for a purification step to remove it. On the other hand, if the content of the siloxane compound represented by formula (3) is less than 0.99 mol, unreacted 5-norbornene-exo-2,3-dicarboxylic anhydride will remain, and effort will be necessary for a purification step to remove it.

The catalyst for the hydrosilylation reaction is not particularly restricted so long as it has hydrosilylating activity. From the viewpoint of excellent catalytic activity, tris(dimethylvinyldisiloxane)diplatinum(0), dichlorobis(triphenylphosphine)platinum(II) and hexachloroplatinic(IV) acid are preferred, and tris(dimethylvinyldisiloxane)diplatinum(0) and dichlorobis(triphenylphosphine)platinum(II) are more preferred. Hexachloroplatinic(IV) acid has high activity, but is usually in hexahydrate form, and therefore moisture is present in the reaction system and the ring of the target tetracarboxylic dianhydride may be hydrolyzed by the water.

Tris(dimethylvinyldisiloxane)diplatinum(0) may be synthesized by the method described in Jikken Kagaku Koza, 5th Edition, Vol. 21, p. 346. It is also available as a xylene solution with a 2% platinum concentration from Aldrich Co. under the trade name "Platinum(0)-1,3-divinyl-1,1,3,3-tetramethyldisiloxane complex", and this may also be used.

The amount of catalyst added is preferably between $2 \times 10^{-5}$ and $2 \times 10^{-3}$ gram atom and more preferably between $5 \times 10^{-5}$ and $5 \times 10^{-4}$ gram atom, as the amount of platinum metal with respect to 1 mol of 5-norbornene-exo-2,3-dicarboxylic anhydride. If the catalyst amount is less than $2 \times 10^{-5}$ gram atom, not only will the reaction rate be retarded but activity may be lost due to impurities in the starting materials, while if it is greater than $2 \times 10^{-3}$ gram atom, there will be presented the risk of runaway exothermic reaction and the reaction mixture will tend to be darker blackish brown, requiring a greater amount of active carbon for decoloration.

The solvent for hydrosilylation reaction may be any one that dissolves the starting materials and catalyst and is inert to the hydrosilylation reaction, and toluene, xylene, chlorobenzene, tetrahydrofuran or the like may be used.

The reaction temperature will normally be 40-100° C. and is preferably 50-90° C. The time required for completion of the reaction will vary depending on the catalyst amount and the reaction temperature, and therefore it is preferably adjusted with sampling analysis by GPC (gel permeation chromatography), but it will usually be about 0.5-10 hours.

When 1,1,3,3-tetramethyldisiloxane is used as the siloxane compound represented by formula (3) in the hydrosilylation reaction, a side reaction represented by the following reaction formula (9) sometimes takes place. The compound represented by chemical formula (9a) below manifests as white crystals with a melting point of 178-179.5° C. The compound represented by chemical formula (9b) is a compound obtained by hydrogenation of a 5-norbornene-exo-2,3-dicarboxylic anhydride represented by chemical formula (2). When a tetracarboxylic dianhydride of the invention in which such compounds are included is used as a starting material for polyimide synthesis, it becomes impossible to increase the molecular weight of the polyimide. In addition, heating to near 180° C. becomes necessary for mixture with an epoxy resin, for use as a curing agent for epoxy resins. The compound is therefore preferably separated and removed from the tetracarboxylic dianhydride.

[Chemical Formula 18]

(9)

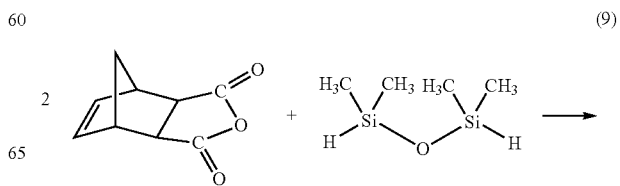

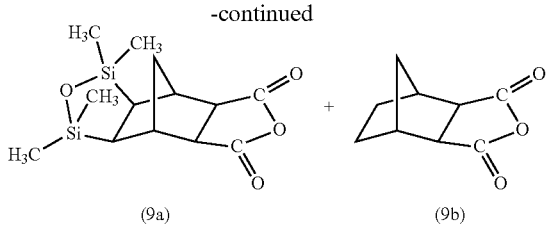

(9a)　　　　　　　　　(9b)

The compound represented by chemical formula (9a) can be removed by extraction. Specifically, the tetracarboxylic dianhydride of this embodiment containing a compound represented by chemical formula (9a) may be heated and stirred after addition of a mixed solvent of hexane and toluene and allowed to stand in a heated state for separation into two phases, and then the compound represented by formula (9a) extracted into the upper layer for removal. The blending ratio of the hexane and toluene is preferably 100:2-100:20, as the weight ratio. The temperature for heating during extraction is preferably 40-70° C. The compound represented by chemical formula (9b) can be removed by distillation under reduced pressure.

An exo-exo type tetracarboxylic dianhydride of the invention has excellent manageability as a liquid, and can therefore be suitably used as a curing agent for epoxy resins, or as a tetracarboxylic dianhydride component for synthesis of a polyimide resin.

The present invention is not in any way limited to the preferred embodiment described above.

EXAMPLES

The present invention will now be explained in detail by examples, with the understanding that the invention is not limited to the examples.
<GPC Measuring Conditions>
The GPC measuring conditions for the examples were as follows.
Equipment: Pump (Model L-6000 by Hitachi, Ltd.), detector (Model L-3300RI by Hitachi, Ltd.)
Column: Two 500 mm Gelpack GL-A110 columns in series (trade name of Hitachi Chemical Co., Ltd.).
Eluent: Tetrahydrofuran
Measuring temperature: 25° C.
Flow rate: 1.0 mL/min
<NMR Measuring Conditions>
The NMR measuring conditions for the examples were as follows.
Equipment: AV400M by Bruker
Solvent: Deuterochloroform
Sample concentration: 80 mg/0.75 mL
Measuring temperature: Room temperature (24° C.)
Resonance frequency: $^1$H NMR: 400.23 MHz, $^{13}$C NMR: 100.64 MHz
Number of scans: $^1$H NMR: 16, $^{13}$C NMR: 128

Synthesis Example 1

Synthesis of 5-norbornene-exo-2,3-dicarboxylic Anhydride Represented by Chemical Formula (2)

In a 1 L four-necked flask equipped with a stirrer, condenser tube and thermometer there was charged 300 g of 5-norbornene-endo-2,3-dicarboxylic anhydride (product of Hitachi Chemical Co., Ltd., melting point: 164.5-166° C., hereunder referred to as "endo-HAC"), and it was heated and stirred at 170° C. for 5 hours. The flask was then allowed to cool, and when it reached 100° C., 300 g of toluene was added and the mixture was stirred and allowed to stand for one night. The precipitated crystals were removed by filtration. The crystal weight was 223 g. Next, 300 g of toluene was added to the crystals, recrystallization was performed, the crystals obtained by recrystallization were vacuum dried and the adhering toluene was removed. The amount of obtained crystals was 156 g and they had a melting point of 146.5-148.5° C. The NMR spectrum was analyzed, confirming that the crystals were 5-norbornene-exo-2,3-dicarboxylic anhydride (hereunder referred to as "exo-HAC").

Example 1

Synthesis of Tetracarboxylic Dianhydride Represented by Chemical Formula (6)

In a 1 L four-necked flask equipped with a stirrer, dropping funnel, condenser tube and thermometer there were charged 240 g of toluene and 123.20 g (0.7505 mol) of exo-HAC, and heating and stirring were initiated. When the temperature in the flask reached 80° C., 2.99 g of a platinum(0)-1,3-divinyl-1,1,3,3-tetramethyldisiloxane complex (xylene solution with 2% platinum concentration) ($3.07 \times 10^{-4}$ gram atom as platinum metal) by Aldrich Co. was added and 50.17 g (0.3735 mol) of 1,1,3,3-tetramethyldisiloxane (hereunder referred to as "TMDS") was slowly added dropwise into the flask through a dropping funnel. Since the reaction temperature increases with dropwise addition of the TMDS, it was added dropwise over a period of one hour while taking care to maintain a temperature of 90° C. in the flask, and then reaction was continued for 1 hour while maintaining a temperature of 90° C. inside the flask. Next, the reaction mixture was cooled, 15 g of active carbon was added and the mixture was stirred at room temperature for 2 hours, after which the active carbon was removed by filtration. A rotary evaporator was used for concentration of the filtrate under reduced pressure, to obtain 166.4 g of a viscous, colorless transparent liquid. As a result of GPC analysis, it was confirmed that none of the toluene used as a solvent was present in the liquid.

Next, extraction for purification were performed to remove the compound represented by chemical formula (9a), as a by-product of the reaction. After charging 86.8 g of the viscous, colorless transparent liquid, 169.4 g of hexane and 23.9 g of toluene into the extraction-end flask of a continuous simple extraction apparatus, there were charged into the distillation-end flask 101.3 g of hexane, and then 60.0 g of hexane through a dropping funnel. Operation was conducted for 10 hours with a water bath temperature of 65° C. at the extraction-end and an oil bath temperature of 115° C. at the distillation-end. When the lower layer in the extraction-end flask was recovered and the solvent therein was removed and weighed, it was found to be 62.0 g. Also, the compound represented by chemical formula (9b), as another by-product component, was removed by distillation while blowing in a trace amount of nitrogen under reduced pressure of 70 Pa.

The target substance 5,5'-exo-(1,1,3,3-tetramethyldisiloxane-1,3-diyl)bisbicyclo[2.2.1] heptan e-exo-2,3-dicarboxylic anhydride represented by chemical formula (6) (hereunder refereed to as "exo-NB-DiSXDA") was thus obtained. The purity of the exo-NB-DiSXDA was 98.3 wt %, and it was a colorless transparent, viscous liquid having a viscosity of 2960 Pa·s at 40° C. and 42500 Pa·s at 25° C., with no visible changes in appearance even after 2 months of storage.

Figure 2:
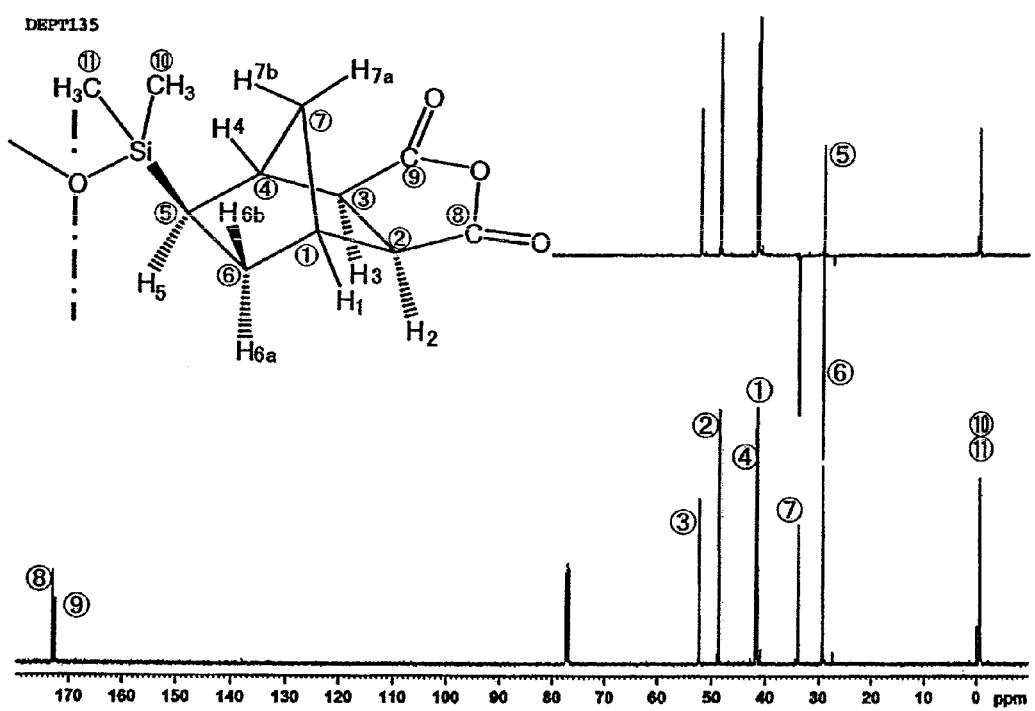
FIG. 2 shows the $^{13}$C-NMR spectrum of the tetracarboxylic dianhydride of Example 1.

By NMR measurement, the obtained exo-NB-DiSXDA was confirmed to have the stereostructure of a tetracarboxylic dianhydride represented by chemical formula (6). FIG. 1 shows the $^1$H-NMR spectrum of the exo-NB-DiSXDA as the tetracarboxylic dianhydride of Example 1. In FIG. 1, the circled numerals indicate the carbon positions, the subscript "a" being used for protons measured at the low frequency end and the subscript "b" being used for protons measured at the high frequency end, for the methylene protons. The dashed lines in the stereostructure are the symmetry lines of the molecule. The integrated intensity ratio reflects the structure. FIG. 2 is a $^{13}$C-NMR spectrum for exo-NB-DiSXDA, and 11 carbon peaks were measured for the structure.

Example 2

Synthesis of Tetracarboxylic Dianhydride Represented by Chemical Formula (7)

In a 1 L four-necked flask equipped with a stirrer, dropping funnel, condenser tube and thermometer there were charged 270 g of toluene and 67.45 g (0.4109 mol) of exo-HAC, and heating and stirring were initiated. When the temperature in the flask reached 50° C., 1.609 g of a platinum(0)-1,3-divinyl-1,1,3,3-tetramethyldisiloxane complex (xylene solution with 2% platinum concentration) ($1.65 \times 10^{-4}$ gram atom as platinum metal) by Aldrich Co. was added and 42.80 g (0.2053 mol) of 1,1,3,3,5,5-hexamethyltrisiloxane (hereunder referred to as "HMTS") was slowly added dropwise into the flask through a dropping funnel. Since the reaction temperature increases with dropwise addition of the HMTS, it was added dropwise over a period of one hour while taking care to maintain a temperature of 55° C. in the flask, and then reaction was continued for 3 hours while maintaining a temperature of 55° C. inside the flask.

When the reaction mixture was analyzed by GPC, the reaction proceeded in a quantitative manner, and the composition was 98.8 wt % of the target substance 5,5'-exo-(1,1,3,3,5,5-hexamethyltrisiloxane-1,5-diyl)bisbicyclo [2.2.1]heptane-exo-2,3-dicarboxylic anhydride (hereunder referred to as "exo-NB-TriSXDA") and 1.2 wt % of the exo-HAC starting material.

After cooling, 13 g of active carbon was added and the mixture was stirred at room temperature for 2 hours, after which the active carbon was removed by filtration. A rotary evaporator was used for concentration of the filtrate under reduced pressure, and then the remaining exo-HAC was removed while blowing in a trace amount of nitrogen under reduced pressure of 70 Pa.

This yielded 109.2 g of the target substance exo-NB-TriSXDA with a purity of 99.6 wt % (containing 0.4 wt % exo-HAC). The obtained exo-NB-TriSXDA was a colorless transparent, viscous liquid having a viscosity of 38.4 Pa·s at 40° C. and 220 Pa·s at 25° C., with no visible changes in appearance even after 2 months of storage.

Figure 3:
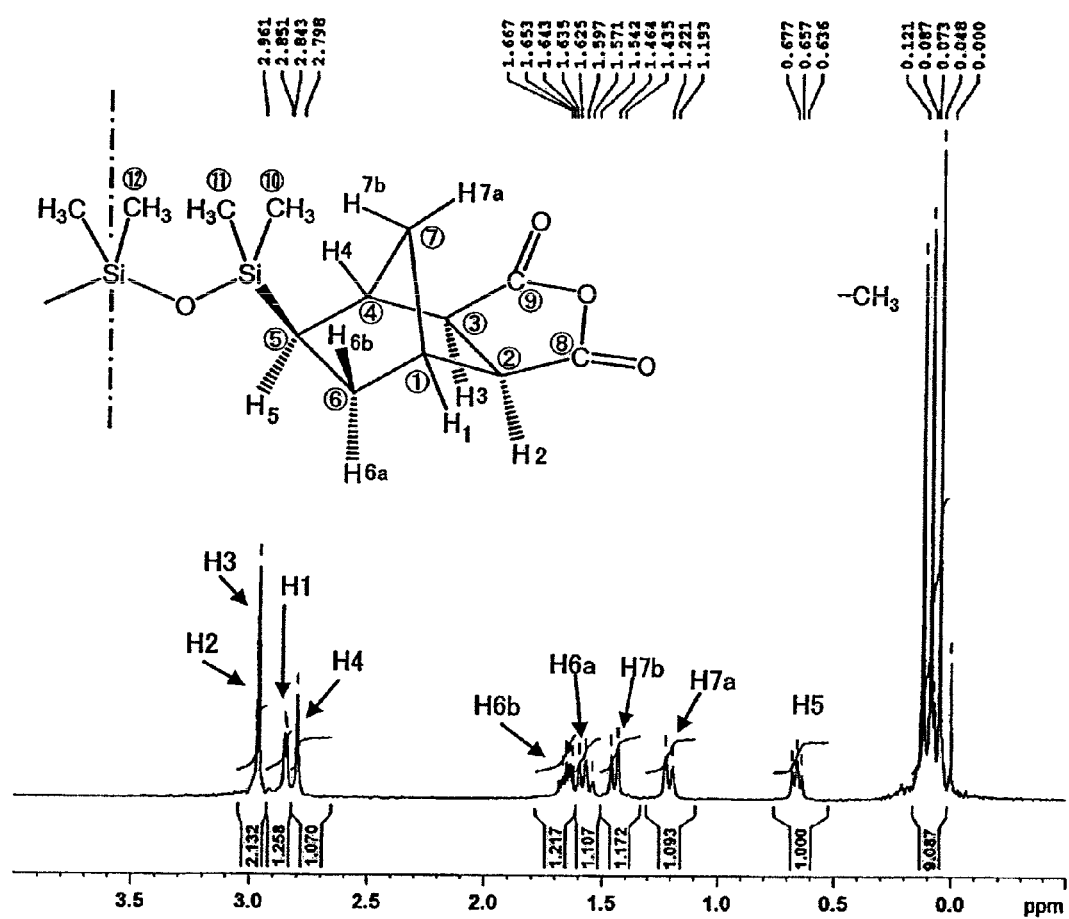
FIG. 3 shows the $^1$H-NMR spectrum of the tetracarboxylic dianhydride of Example 2.
Figure 4:
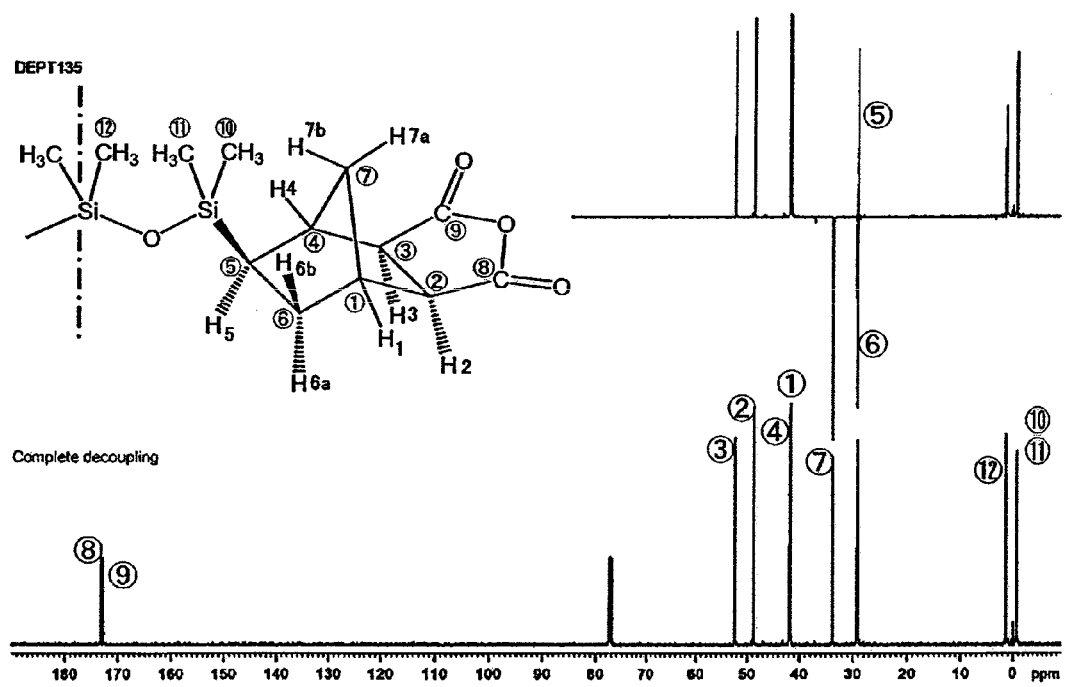
FIG. 4 shows the $^{13}$C-NMR spectrum of the tetracarboxylic dianhydride of Example 2.

By NMR measurement, the obtained exo-NB-TriSXDA was confirmed to have the stereostructure of a tetracarboxylic dianhydride represented by chemical formula (7). FIG. 3 shows the $^1$H-NMR spectrum of the exo-NB-TriSXDA as the tetracarboxylic dianhydride of Example 2. In FIG. 3, the circled numerals indicate the carbon positions, the subscript "a" being used for protons measured at the low frequency end and the subscript "b" being used for protons measured at the high frequency end, for the methylene protons. The dashed lines in the stereostructure are the symmetry lines of the molecule. The integrated intensity ratio reflects the structure. FIG. 4 is a $^{13}$C-NMR spectrum for exo-NB-TriSXDA, and 12 carbon peaks were measured for the structure.

Example 3

Synthesis of Tetracarboxylic Dianhydride Represented by Chemical Formula (8)

In a 200 mL four-necked flask equipped with a stirrer, dropping funnel, condenser tube and thermometer there were charged 79 g of toluene and 11.29 g (0.06878 mol) of exo-HAC, and heating and stirring were initiated. When the temperature in the flask reached 65° C., 0.280 g of a platinum(0)-1,3-divinyl-1,1,3,3-tetramethyldisiloxane complex (xylene solution with 2% platinum concentration) ($2.87 \times 10^{-5}$ gram atom as platinum metal) by Aldrich Co. was added and 12.27 g (0.03439 mol) of 1,1,3,3,5,5,7,7,9,9-decamethylpentasiloxane (hereunder referred to as "DMPS") was slowly added dropwise into the flask through a dropping funnel. Since the reaction temperature increases with dropwise addition of the DMPS, it was added dropwise over a period of 0.5 hour while taking care to maintain a temperature of 65° C. in the flask, and then reaction was continued for 7 hours while maintaining a temperature of 65° C. inside the flask.

When the reaction mixture was analyzed by GPC, the reaction proceeded in a quantitative manner, and the composition was 97.1 wt % of the target substance 5,5'-exo-(1,1,3,3,5,5,7,7,9,9-decamethylpentasiloxane-1,9-diyl)bisbicyclo [2.2.1]heptane-exo-2,3-dicarboxylic anhydride (hereunder referred to as "exo-NB-PentaSXDA") and 2.9 wt % of the exo-HAC starting material.

After cooling, 2.5 g of active carbon was added and the mixture was stirred at room temperature for 2 hours, after which the active carbon was removed by filtration. A rotary evaporator was used for concentration of the filtrate under reduced pressure, and then the remaining exo-HAC was removed while blowing in a trace amount of nitrogen under reduced pressure of 70 Pa.

This yielded 21.8 g of the target substance exo-NB-PentaSXDA with a purity of 99.2 wt % (containing 0.8 wt % exo-HAC). The obtained exo-NB-PentaSXDA was a colorless transparent, viscous liquid having a viscosity of 3.95 Pas at 25° C., with no visible changes in appearance even after 2 months of storage.

Figure 5:
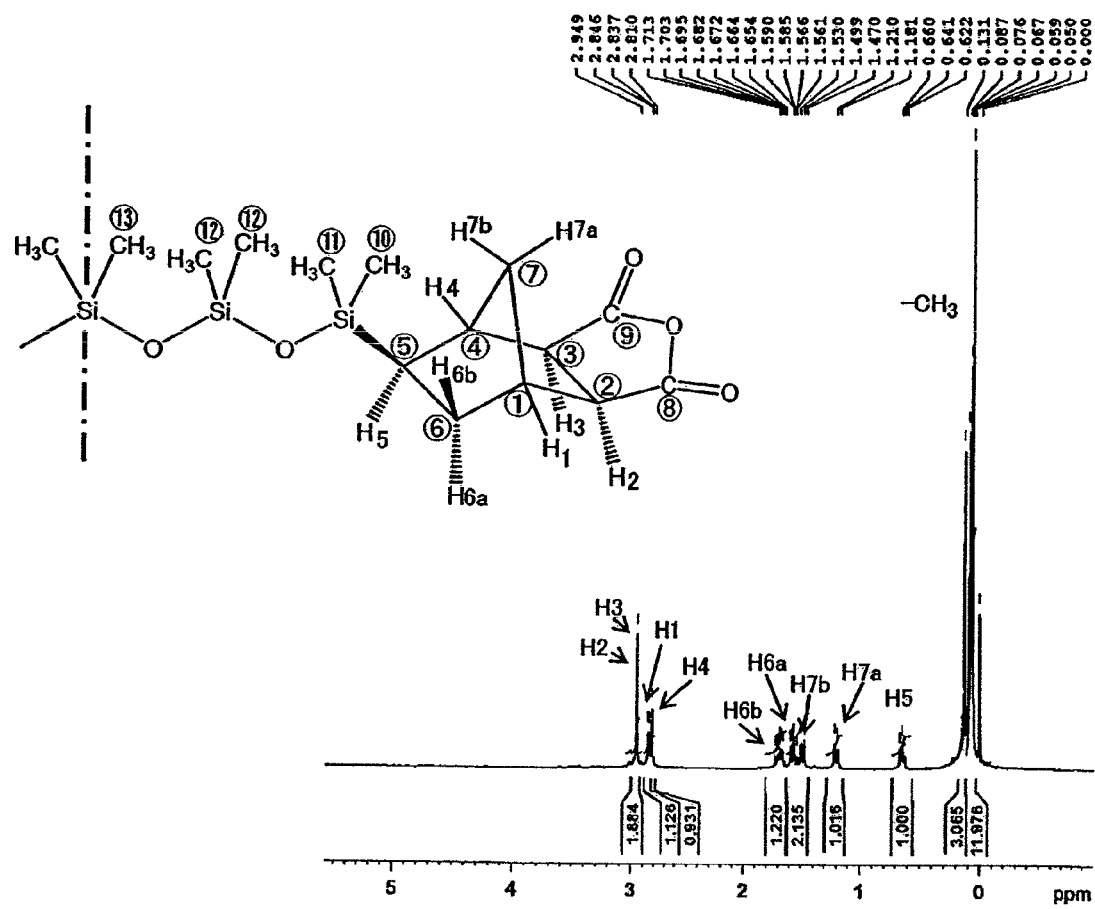
FIG. 5 shows the $^1$H-NMR spectrum of the tetracarboxylic dianhydride of Example 3.
Figure 6:
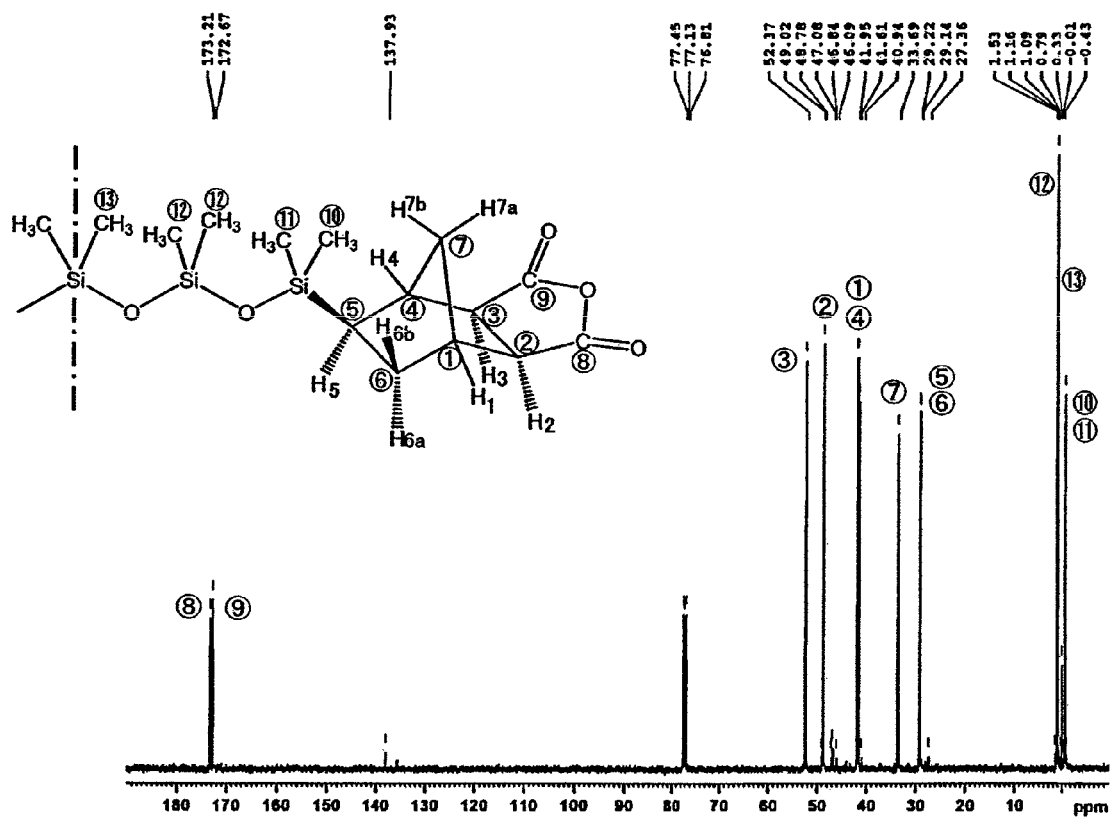
FIG. 6 shows the $^{13}$C-NMR spectrum of the tetracarboxylic dianhydride of Example 3.

By NMR measurement, the obtained exo-NB-PentaSXDA was confirmed to have the stereostructure of a tetracarboxylic dianhydride represented by chemical formula (8). FIG. 5 shows the $^1$H-NMR spectrum of the exo-NB-PentaSXDA as the tetracarboxylic dianhydride of Example 3. In FIG. 5, the circled numerals indicate the carbon positions, the subscript "a" being used for protons measured at the low frequency end and the subscript "b" being used for protons measured at the high frequency end, for the methylene protons. The dashed lines in the stereostructure are the symmetry lines of the molecule. The integrated intensity ratio reflects the structure. FIG. 6 is a $^{13}$C-NMR spectrum for exo-NB-PentaSXDA, and 13 carbon peaks were measured for the structure.

Example 4

Synthesis of Tetracarboxylic Dianhydride Represented by Chemical Formula (10)

[Chemical Formula 19]

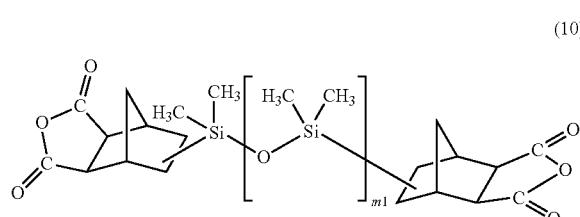

(10)

In formula (10), the average for m1 is 3.8.

In a 300 mL four-necked flask equipped with a stirrer, dropping funnel, condenser tube and thermometer there were charged 90 g of toluene and 42.68 g (0.2599 mol) of exo-HAC, and heating and stirring were initiated. When the temperature in the flask reached 65° C., 1.05 g of a platinum(0)-1,3-divinyl-1,1,3,3-tetramethyldisiloxane complex (xylene solution with 2% platinum concentration) ($1.08 \times 10^{-4}$ gram atom as platinum metal) by Aldrich Co. was added and 45.63 g (0.1278 mol) of a siloxane oligomer represented by chemical formula (11) below (a mixture wherein m1 is 2-9, the average of m1 being 3.8) was slowly added dropwise into the flask through a dropping funnel. Since the reaction temperature increases with dropwise addition of the siloxane oligomer, it was added dropwise over a period of one hour while taking care to maintain a temperature of 65° C. in the flask, and then reaction was continued for 2 hours while maintaining a temperature of 65° C. inside the flask.

[Chemical Formula 20]

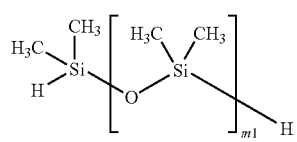

(11)

When the reaction mixture was analyzed by GPC, the reaction proceeded in a quantitative manner, and the composition was 98.8 wt % of the dimethylsiloxane oligomer represented by chemical formula (10) (hereunder referred to as "exo-NB-nSXDA (n=4.8)") and 1.2 wt % of the exo-HAC starting material.

After cooling, 7.8 g of active carbon was added and the mixture was stirred at room temperature for 1 hour, after which the active carbon was removed by filtration. A rotary evaporator was used for concentration of the filtrate under reduced pressure, and then the remaining exo-HAC was removed while blowing in a trace amount of nitrogen under reduced pressure of 70 Pa.

This yielded 83.2 g of the target substance exo-NB-nSXDA (n=4.8). The obtained exo-NB-nSXDA (n=4.8) was a colorless transparent liquid with a viscosity of 5.94 Pa·s at 25° C., and the refractive index at 25° C. was 1.4734. No changes in outer appearance were seen even with storage for 2 months.

Example 5

Synthesis of Tetracarboxylic Dianhydride Represented by Chemical Formula (12)

[Chemical Formula 21]

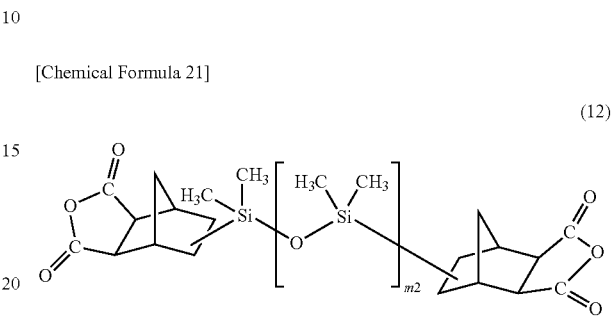

(12)

In formula (12), the average for m2 is 13.0.

In a 300 mL four-necked flask equipped with a stirrer, dropping funnel, condenser tube and thermometer there were charged 60 g of toluene and 33.65 g (0.205 mol) of exo-HAC, and heating and stirring were initiated. When the temperature in the flask reached 65° C., 0.82 g of a platinum(0)-1,3-divinyl-1,1,3,3-tetramethyldisiloxane complex (xylene solution with 2% platinum concentration) ($8.4 \times 10^{-5}$ gram atom as platinum metal) by Aldrich Co. was added and 95.23 g (0.100 mol) of a siloxane oligomer represented by chemical formula (13) below (a mixture wherein m2 is 6-22, the average of m2 being 13.0) was slowly added dropwise into the flask through a dropping funnel. Since the reaction temperature increases with dropwise addition of the siloxane oligomer, it was added dropwise over a period of 1.5 hours while taking care to maintain a temperature of 65° C. in the flask, and then reaction was continued for 2 hours while maintaining a temperature of 65° C. inside the flask.

[Chemical Formula 22]

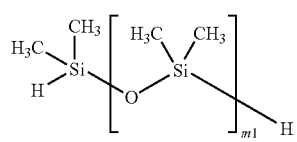

(13)

When the reaction mixture was analyzed by GPC, the reaction proceeded in a quantitative manner, and the composition was 99.2 wt % of the dimethylsiloxane oligomer represented by chemical formula (12) (hereunder referred to as "exo-NB-nSXDA (n=14)") and 0.8 wt % of the exo-HAC starting material.

After cooling, 6.1 g of active carbon was added and the mixture was stirred at room temperature for 1 hour, after which the active carbon was removed by filtration. A rotary evaporator was used for concentration of the filtrate under reduced pressure, and then the remaining exo-HAC was removed while blowing in a trace amount of nitrogen under reduced pressure of 70 Pa.

This yielded 123.6 g of the target substance exo-NB-nSXDA (n=14). The obtained exo-NB-nSXDA (n=14) was a colorless transparent liquid with a viscosity of 0.397 Pa·s at 25° C., and the refractive index at 25° C. was 1.4402. No changes in outer appearance were seen even with storage for 2 months.

Comparative Example 1

Synthesis of Tetracarboxylic Dianhydride Represented by Chemical Formula (4a)

In a 1 L four-necked flask equipped with a stirrer, dropping funnel, condenser tube and thermometer there were charged 200 g of toluene and 82.08 g (0.5000 mol) of endo-HAC, and heating and stirring were initiated. When the temperature in the flask reached 80° C., 2.01 g of a platinum(0)-1,3-divinyl-1,1,3,3-tetramethyldisiloxane complex (xylene solution with 2% platinum concentration) ($2.06 \times 10^{-4}$ gram atom as platinum metal) by Aldrich Co. was added and 33.55 g (0.2498 mol) of TMDS was slowly added dropwise into the flask through a dropping funnel. Since the reaction temperature increases with dropwise addition of the TMDS, it was added dropwise over a period of one hour while taking care to maintain a temperature of 90° C. in the flask, and then reaction was continued for 6 hours while maintaining a temperature of 90° C. inside the flask.

When the reaction mixture was analyzed by GPC, the composition was 87.0 wt % of 5,5'-exo-(1,1,3,3-tetramethyldisiloxane-1,3-diyl)bisbicyclo[2.2.1] heptane-endo-2,3-dicarboxylic anhydride (hereunder referred to as "endo-NB-DiSXDA"), 6.3 wt % of a compound of chemical formula (9a) wherein the dicarboxylic anhydride groups were in the endo-configuration with respect to the norbornane ring, and 6.8 wt % of a mixture of the endo-HAC starting material and its hydrogenated form, norbornane-endo-2,3-dicarboxylic anhydride.

Next, the reaction mixture was cooled, 15 g of active carbon was added and the mixture was stirred at room temperature for 2 hours, after which the active carbon was removed by filtration. A rotary evaporator was used for concentration of the filtrate under reduced pressure to 130 g, and then 183 g of diethyl ether was added and the mixture was allowed to stand for one night. The crystals precipitating on the container wall were removed out, rinsed with diethyl ether and dried, and the weight was measured to be 81.6 g. The melting point of the crystals was 135.5–159° C. NMR measurement confirmed the crystals to be endo-NB-DiSXDA.

<Preparation of Epoxy Resin Composition>

The tetracarboxylic dianhydrides obtained in the examples and comparative examples were each mixed with 100 parts by weight of a bisphenol A-type epoxy resin (trade name: jER828 by Japan Epoxy Resins Co., Ltd.) in the amounts listed in Table 1, to prepare epoxy resin compositions.

(Viscosity Measurement)

The viscosity of each of the prepared epoxy resin compositions at 25° C. was measured using an EHD-type viscometer (product of Tokyo Keiki Kogyo Co., Ltd.). The viscosity of "jER828" alone was 13.2 Pa·s.

TABLE 1

| Tetracarboxylic dianhydride | Content*[1] (parts by wt.) | Mixing temperature*[2] (° C.) | Viscosity (Pa·s) |
|---|---|---|---|
| Example 1 | exo-NB-DiSXDA | 106 | 60 | 1030 |
| Example 2 | exo-NB-TriSXDA | 123 | 40 | 66 |
| Example 3 | exo-NB-PentaSXDA | 157 | 20 | 5.3 |
| Comp. Example 1 | endo-NB-DiSXDA | 106 | 150 | 870 |

*[1] Addition at 0.85 equivalent of dicarboxylic anhydride groups of the tetracarboxylic dianhydride with respect to one equivalent of epoxy groups.
*[2] Heating temperature necessary to obtain a uniform epoxy resin mixture.

As clearly seen in Table 1, the tetracarboxylic dianhydrides of the invention were compatible with the epoxy resin without heating to a high temperature exceeding 100° C., and were therefore easily manageable. On the other hand, the tetracarboxylic dianhydride of Comparative Example 1 did not dissolve in the epoxy resin even with heated mixing at 100° C. for 1 hour, and heating to 150° C. (the melting point of tetracarboxylic dianhydride) was necessary.

By using a tetracarboxylic dianhydride of the invention it is possible to lower the heating temperature during preparation of an epoxy resin composition, and thereby avoid altering the curing reaction of the epoxy resin composition.

INDUSTRIAL APPLICABILITY

According to the invention it is possible to provide a silicon-containing tetracarboxylic dianhydride having a norbornane skeleton, which is liquid at room temperature and has excellent manageability, as well as a process for preparation of the same. The tetracarboxylic dianhydride of the invention can be suitably used as a curing agent for epoxy resins, or as a tetracarboxylic dianhydride component for synthesis of polyimide resins.

The invention claimed is:

1. A tetracarboxylic dianhydride represented by the following formula (1).

[Chemical Formula 1]

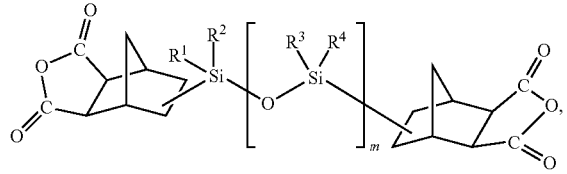

(1)

wherein in formula (1), $R^1$, $R^2$, $R^3$ and $R^4$ each independently represent an alkyl group having from 1 to 5 carbon atoms, and m represents a number from 1 to 30; all of the silicon atoms bonding to the norbornane rings in formula (1) are in an exo-configuration with respect to the norbornane rings, and all of the dicarboxylic anhydride groups bonding to the norbornane rings are in an exo-configuration with respect to the norbornane rings, and wherein the tetracarboxylic dianhydride represented by the following formula (1) has a viscosity of 0.1–45000 Pa·s at 25° C.

2. A process for preparation of the tetracarboxylic dianhydride according to claim 1, the process comprising:
    a step of hydrosilylation reaction between a 5-norbornene-exo-2,3-dicarboxylic anhydride represented by the following chemical formula (2) and a siloxane compound represented by the following formula (3).
[Chemical Formula 2]
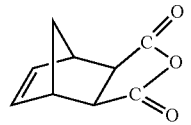
(2)
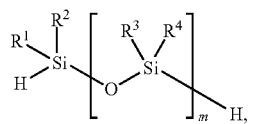
(3)
wherein in formula (3), $R^1$, $R^2$, $R^3$ and $R^4$ each independently represent an alkyl group having from 1 to 5 carbon atoms, and m represents a number from 1 to 30.
* * * * *